United States Patent
Campbell

(10) Patent No.: US 8,569,375 B2
(45) Date of Patent: Oct. 29, 2013

(54) COMPOSITIONS

(75) Inventor: Alistair Campbell, Hull (GB)

(73) Assignee: Reckitt Benckiser Healthcare (UK) Limited, Slough, Berkshire (GB)

( * ) Notice: Subject to any disclaimer, the term of this patent is extended or adjusted under 35 U.S.C. 154(b) by 174 days.

(21) Appl. No.: 13/059,260

(22) PCT Filed: Aug. 18, 2009

(86) PCT No.: PCT/GB2009/002014
§ 371 (c)(1), (2), (4) Date: Mar. 25, 2011

(87) PCT Pub. No.: WO2010/020772
PCT Pub. Date: Feb. 25, 2010

(65) Prior Publication Data
US 2011/0201685 A1    Aug. 18, 2011

(30) Foreign Application Priority Data

Aug. 22, 2008 (GB) .................................. 0815405.6
Jan. 9, 2009 (GB) .................................. 0900288.2

(51) Int. Cl.
*A61K 31/19* (2006.01)
(52) U.S. Cl.
USPC ........................................................ 514/570
(58) Field of Classification Search
USPC ........................................................ 514/570
See application file for complete search history.

(56) References Cited

U.S. PATENT DOCUMENTS 6,287,600 B1 * 9/2001 Ouali et al. .................... 424/472
2008/0014290 A1 * 1/2008 Jones ............................ 424/682

FOREIGN PATENT DOCUMENTS

WO    WO9629986    * 2/1996
WO    WO2007110871 * 10/2007

OTHER PUBLICATIONS

Pourali et al. CAS: 156: 73968, 2011.*

* cited by examiner

*Primary Examiner* — Rei-tsang Shiao
(74) *Attorney, Agent, or Firm* — Troutman Sanders LLP; Ryan A. Schneider

(57) ABSTRACT

An ingestible particulate composition comprises: a) at least one compound selected from the group consisting of 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine; and b) one or more bioadhesive materials. Resulting particulate compositions have excellent flow characteristics, dust suppression, organoleptic properties and stability. They are highly suitable for administration direction into a patient's mouth, and ingested to alleviate the symptoms of a sore throat.

17 Claims, 6 Drawing Sheets

COMPOSITIONS

CROSS-REFERENCE TO RELATED APPLICATIONS

This application is a US National Stage of International Application No. PCT/GB2009/002014, filed 18 Aug. 2009, which claims the benefit of both GB 0900288.2, filed 9 Jan. 2009, and GB 0815405.6, filed 22 Aug. 2008.

The present invention relates to pharmaceutical compositions, and in particular to pharmaceutical compositions for the treatment of sore throats.

BACKGROUND OF THE INVENTION

Sore throats are often treated by sucking a sugar-based lozenge. The lozenge contains at least one compound which is active against sore throats. In addition, the sucking action results in the production of saliva which lubricates the throat and reduces the pain and discomfort experienced by an individual.

A boiled sugar lozenge is a 'glass' or supercooled liquid, and at extremely high viscosity has an amorphous non-crystalline state. In this state, other constituents can be dissolved or suspended (colours, flavours, pharmacological actives etc). The moisture content of such a lozenge is low (c. 2%). Some of this moisture is in a 'free' state, but much of the moisture is not. This gives a stable chemical and physical environment.

However, small increases in the moisture content of such lozenges have the following detrimental effects. The viscosity of the 'glass' is reduced, which leads to a gradual 'cold flow' of the lozenge. The presence of 'free' water provides a reaction medium in which accelerated degradation of added components can occur. Water causes the lozenge to become sticky and both unattractive and difficult to handle by packing equipment or by the user. Water is involved in hydrolysis of the disaccharide bond in sugar, catalysed under acid conditions provided by the typical inclusion of flavour enhancing organic acids. Cleavage of the disaccharide bond forms glucose and fructose, which are both more hygroscopic than sugar (sucrose) and tend to accelerate the absorption of further water from the surrounding environment. The reduction in the sugar content compromises the physical hardness of the lozenge. In some cases complete liquefaction of the lozenge can occur. As the absorption of water is an accelerative process, low initial water content and the exclusion of even small quantities of water from the lozenge environment are important to maximise shelf life. For a medicated lozenge containing pharmaceutical ingredients, the issue of stability is particularly significant as compared to confectionery lozenges. For example, a much longer shelf life required of medicinal products, the health risks associated with chemical change mediated by increased water content, and the higher value of the goods spoiled.

It would, therefore, be desirable to develop an alternative product for treating sore throats which avoids the use of a sugar-based lozenge.

BRIEF SUMMARY OF THE INVENTION

In the present invention it is an important object of preferred embodiments to achieve a flowable particulate composition which can be administered directly into the mouth. The issues surrounding the oral administration of lozenges are quite different to the issues surrounding the oral administration of particulate compositions, for example lozenges may simply be swallowed or more preferably may be sucked. Sucking stimulates the release of saliva, which can lubricate the throat reducing the pain and discomfort, or the perception thereof. When a particulate composition is administered it potentially has a rapid drying effect in the mouth, and there is no sucking to mitigate that effect.

The development objective of this formulation was to produce a granule format as a delivery method for suitable pharmaceutically active compounds in order to give localised pain relief and reduce inflammation in the throat. Although, some granular compositions are known these do not include a bioadhesive and are rapidly washed away from the throat.

In accordance with a first aspect of the present invention there is provided an ingestible particulate composition comprising:

a) at least one compound selected from the group consisting of 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine; and b) one or more bioadhesive materials.

Preferably the composition is a flowable particulate, by which we mean that it may be poured from a container, e.g. a sachet, in the manner of sugar or salt.

Preferred one or more compounds include but are not limited to 2,4-dichlorobenzyl alcohol, amylmetacresol, hexylresorcinol, and flurbiprofen and combinations thereof. In a preferred embodiment the at least one pharmaceutically active compound is selected from flurbiprofen.

The compositions of the present invention can also comprise a bicarbonate and/or an organic acid. The composition of the present invention may effervesce in the mouth of the patient; the bicarbonate, and the organic acid, preferably forming an effervescent couple.

Examples of bicarbonates are alkali metal bicarbonates such as sodium and potassium bicarbonate and alkaline earth metal bicarbonates. One or more different bicarbonates may be used.

The bicarbonate when present is suitably present in the compositions of the present invention in an amount up to 15%, preferably 5 to 10 wt %; this being the cumulative amount when there is more than one bicarbonate present.

Preferably the organic acid is a carboxylic acid. Most preferably it is a polycarboxylic acid. Preferably it has 2-5 carboxylic acid groups, more preferably 3-4 carboxylic acid groups, especially 3. Examples of preferred organic acids include citric acid, tartaric acid, malic acid, succinic acid, ascorbic acid, adipic acid and fumaric acid.

The molar ratio of organic acid(s):bicarbonate (combined weight when more than one is present) can be:

3 (acid):1 (bicarbonate);
2 (acid):1 (bicarbonate);
1 (acid):1 (bicarbonate);
1 (acid):greater than 1 (bicarbonate);
1 (acid):at least 1.5 (bicarbonate);
1 (acid):at least 2 (bicarbonate); and
1 (acid):3 (bicarbonate).

A preferred effervescent couple is sodium bicarbonate and citric acid.

Preferably the particulate composition contains at least 0.3 wt % organic acid, more preferably at least 1 wt %, more preferably at least 2 wt %, and most preferably 2.5 wt %. These values denote the cumulative amount when there is more than one organic acid present; and are based on total weight of the composition.

Suitably the one or more bioadhesive materials is a polymeric or oligomeric compound; preferably a polymeric or oligomeric compound having a high molecular weight up to several million Daltons.

Preferred one or more bioadhesive materials are selected from the group comprising carbomers, such as Carbopol 974P and Carbopol 941P, xanthan gums, locust bean gum, alginate, carageenan, or cellulose. Other suitable carbomers can be used.

Preferred compositions of the invention do not contain a polyvinyl pyrrolidone, or acacia.

The one or more bioadhesive materials is preferably present in an amount up to 10 wt %, preferably up to 5 wt %, most preferably up to 3 wt %. In each case these definitions denote the cumulative amount when there is more than one bioadhesive material present; and are based on the total amount of the components.

The compositions of the present invention may also comprise further optional components.

The compositions of the present invention may also comprise one or more diluents, one or more colourings, sweetenings, flavourings, pH adjusting ingredients, fillers, flow aids, preservatives, antioxidants, moisture scavengers, colourants and processing aids. Other suitable excipients can also be included. When the compositions of the present invention are intended for use as sustained releasing compositions they will also comprise at least one active ingredient suitable for specific delivery to the stomach, such as a drug. Preferred diluents are xylitol, and/or mannitol, and/or isomalt, and/or sucrose. Preferred sweeteners include aspartame. Preferred flavours include peppermint and coolmix for mint powder. A preferred excipient is a salt such as sodium chloride, potassium chloride.

Preferably the compositions of the invention do not contain chloestyramine.

Preferably, of course, all components of the invention are ingestible, and deemed acceptable by regulation authorities.

Preferably the compositions do not contain magnesium stearate. More preferably they do not contain any stearates or hydrogenated fats. Preferably they do not contain any press aids, or mould release agents. Preferably they do not contain any tabletting aids. Preferably they do not contain apatite, including carbonated apatite.

Preferred compositions of the present invention remain in a flowable form, permitting them to be dispensed straight into the mouth e.g. by spoon or by pouring. Preferably they are in a powder and/or granule form. Preferably they may be regarded as a mixture of powder and granules. Even if they comprise powder they preferably substantially do not release dust into the air. Thus they are preferably without propensity to cause coughing or choking due to inhalation.

Preferably the mean particle size of the composition as determined using sieve methods is not greater than 1.0 mm, and is preferably not greater than 0.5 mm. Preferably it is at least 0.1 mm. Preferably the particulate composition used in the present invention has substantially no particles which would not pass through a 1 mm standard sieve.

Preferably the composition is provided with a flow-aid. Typically the flow aid is silicon dioxide.

In a further aspect of the present invention there is provided a single-pack dosage form (which may otherwise be called a unit dosage pack) containing a single dose of a composition in accordance with the first or second aspect of the present invention. A single pack dosage form could be an ampoule or may be provided by a well of a blister pack, but is preferably a sachet.

Preferably a single-pack dosage form for use in the present invention contains from 0.5 to 2 grams of composition, more preferably from 0.75 to 1 grams.

Most preferably the single-pack dosage form is adapted to dispense its contents to a point or small area within the mouth, preferably on the tongue, rather than to a wide area. Thus it is preferably a pack which may also be termed a targeted outlet pack. It may, for example, be a tubular ampoule, but is preferably a stick-form sachet. Stick-form sachets are available for food products e.g. sauces and soluble coffee granules. A stick-form sachet comprises, essentially, a slim envelope or tube, preferably formed of flexible material, and sealed at its ends. One end is removed (e.g. torn off) by the user, who can then dispense its contents through the open end e.g. using a pouring action. Preferably a suitable stick-pack sachet has an aspect ratio of at least 2, more preferably at least 3, and most preferably at least 5 (whereas a conventional sachet may have an aspect ratio of, typically, 1.3). Aspect ratio is defined for the purpose of this specification as the ratio of the length of the sachet to the maximum width in its central region (away from the sealed ends) measured when the stick-pack sachet is loaded with its intended single dose of composition of the invention (i.e. the diameter, when the stick-pack sachet is in a cylindrical form).

Alternatively the composition could be provided in a bulk pack containing a composition of the invention together with dosage metering information or means (for example a scoop or dosing cup).

In accordance with a further aspect of the present invention there is provided a targeted outlet pack which necessarily deposits the composition onto a small area within the mouth, and containing a single dose of an ingestible particulate composition as defined in the first aspect.

The targeted outlet pack may be further defined in accordance with the preceding paragraphs, and is preferably a stick-pack sachet.

In accordance with a further aspect of the present invention there is provided a composition of the invention as defined herein for use in a method of treatment of the human or animal body by therapy.

A composition of the present invention may thus be used in a method of treatment of the human or animal body by therapy, especially in the treatment of sore throats.

The composition of the present invention may be used in the manufacture of a medicament for the treatment of sore throats or for use as a sustained releasing or targeted delivery composition.

The composition of the present invention may be used in a method of treating sore throats or for sustained releasing or targeting a delivery composition, which comprises orally administering to a subject in need thereof or liable to need an effective amount of the composition.

The composition is generally administered in an amount of from 1 to 100, preferably 5 to 50 mg, more preferably 5-15 mg of pharmaceutical active, per dose.

The composition of the present invention is preferably flowable, substantially without clumping, and substantially without releasing powdery or dusty materials which might induce coughing. Any tendency to become overly sticky in the mouth appears to be reduced by the fact that it is not powdery, and by the fact that the acid and/or the effervescence it causes stimulates the release of saliva, and aids dispersion by agitation, preventing clumping. In addition, it is believed that the production of effervescence assists in the formulation sticking/adhering to a user's throat. In the embodiment of the invention which employs a stick-pack article, or another means for directing the particulate composition onto a particular region of the tongue, there is a further benefit; administering the particulate material to large areas of the mouth surfaces is detrimental in terms of the user's perception of the pleasantness of the experience: a large part of the mouth may thereby become gummy.

The compositions of the present invention may be prepared by mixing the ingredients. It is especially preferred to mix certain components together in particulate form and then granulate them using a suitable granulating agent such as water, a $C_2$-$C_4$ alcohol such as ethanol or isopropanol, or a mixture thereof, before adding the remaining components. Other granulating agents may be used, and cellulose derivatives such as HPMC and starch paste. A preferred starch paste uses water as the granulating solvent. $C_2$-$C_5$ polyols or grades of polyalkylene glycol may also be used as granulating agents.

Components which are suitably granulated in this way are the pharmaceutically active component, the bicarbonate, the one or more bioadhesive materials and the diluents.

In a yet further aspect of the present invention there is provided the use of a bioadhesive material to retain a particulate composition which comprises a pharmaceutically active compound in the oral cavity.

The pharmaceutically active compound can be selected from the group comprising 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine. Particularly preferred compounds are 2,4-dichlorobenzyl alcohol, amylmetacresol, hexylresorcinol and flurbiprofen.

Preferred one or more bioadhesive materials are selected from the group comprising carbomers, such as Carbopol 974P and Carbopol 941P, xanthan gums, locust bean gum, alginate, carageenan, or cellulose. Other suitable carbomers can be used.

In a yet further embodiment there is provided a method of improving the local effect of a pharmaceutically active compound by administering to an individual a particulate composition which comprises a pharmaceutically active compound and a bioadhesive material.

The pharmaceutically active compound can be selected from the group comprising 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine. Particularly preferred compounds are 2,4-dichlorobenzyl alcohol, amylmetacresol, hexylresorcinol and flurbiprofen.

Preferred one or more bioadhesive materials are selected from the group comprising carbomers, such as Carbopol 974P and Carbopol 941P, xanthan gums, locust bean gum, alginate, carageenan, or cellulose. Other suitable carbomers can be used.

In the context of the present application a bioadhesive material is water-swellable, but water-insoluble, and adheres to a surface such as a mucus membrane or skin tissue. The water used for swelling, may be provided by the body of the treated animal, such as by gastric fluid or by mucosal secretions such as saliva.

BRIEF DESCRIPTION OF THE DRAWINGS

The present invention is further described in the following Examples and Figure in which.

DETAILED DESCRIPTION OF PREFERRED EMBODIMENTS

Examples

Figure 1:
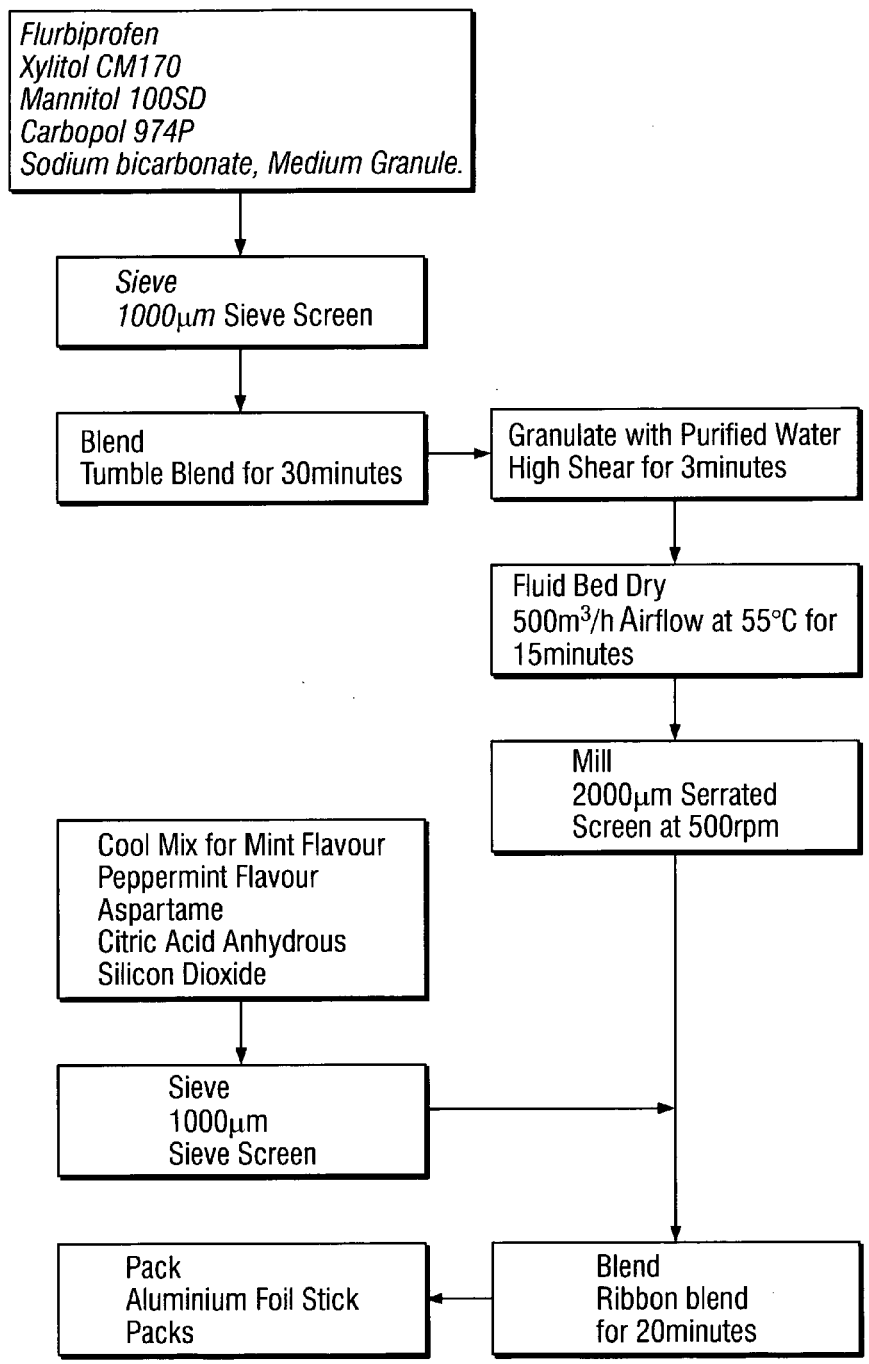
FIG. 1 illustrates a process for preparing the formulation of the present invention.
Figure 2:
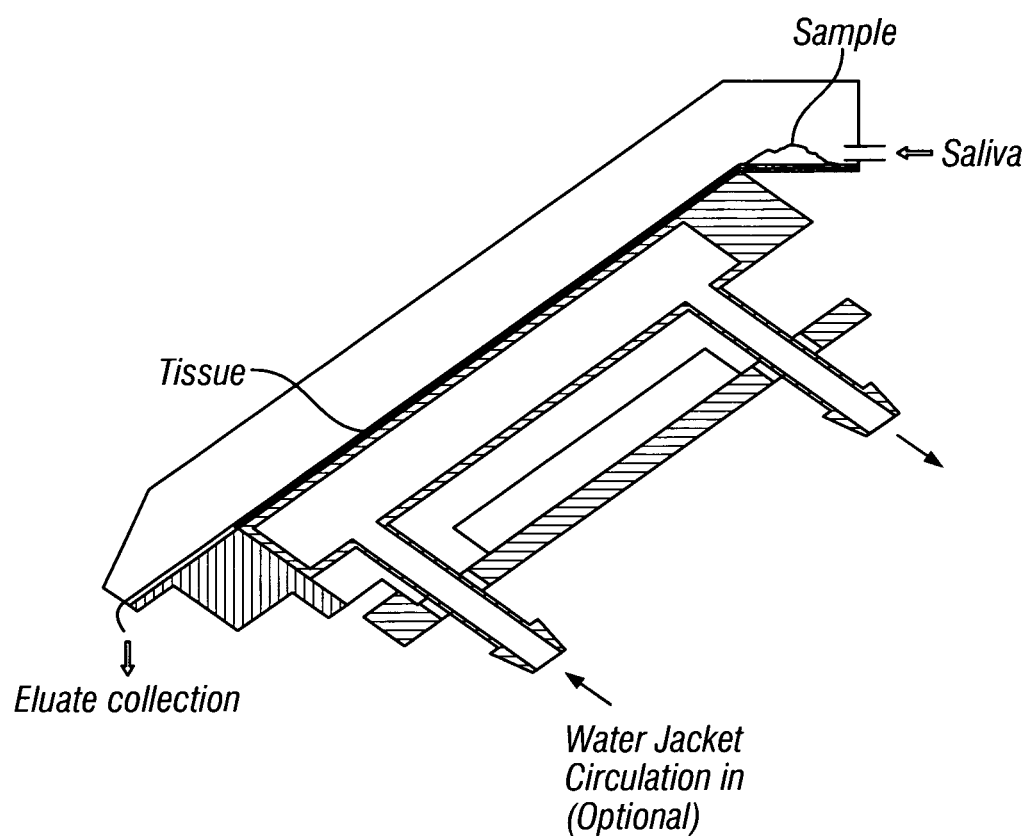
FIG. 2 illustrates the IVOR model used to determine the improvement in bioadhesion of the present invention.
Figure 3:
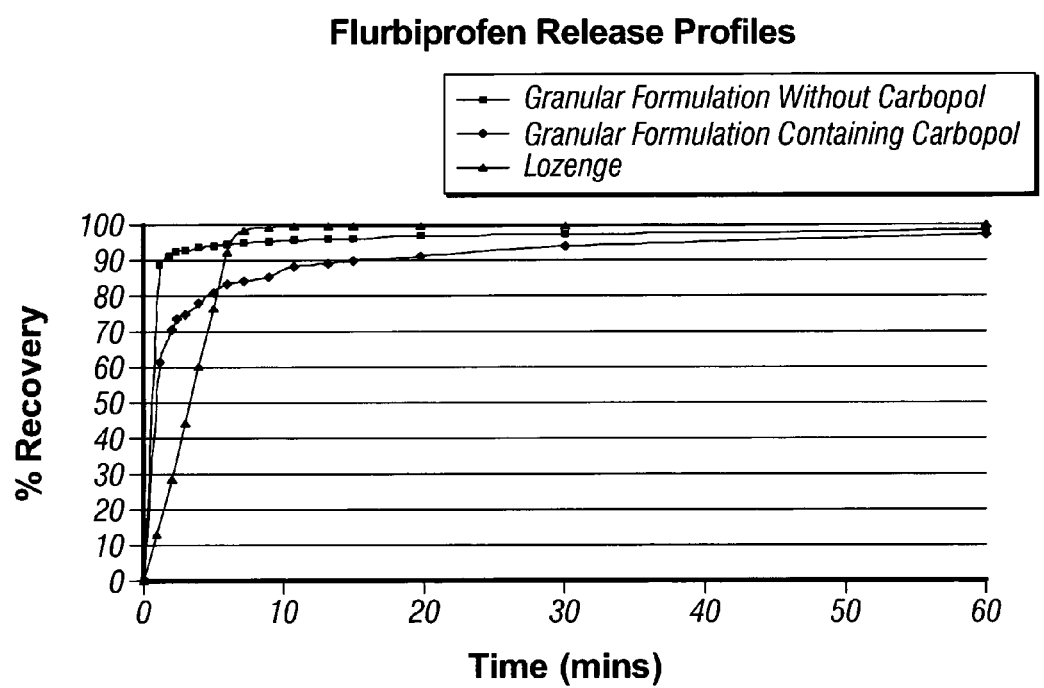
FIG. 3 illustrates the in vitro flurbiprofen-release data obtained.
Figure 4A:
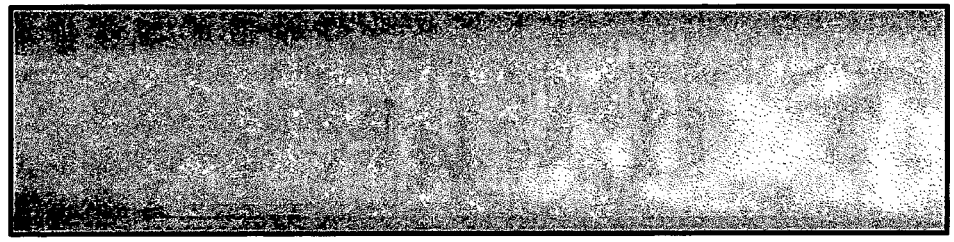
FIG. 4a illustrates the image obtained for a non-Carbopol containing formulation.
Figure 4B:
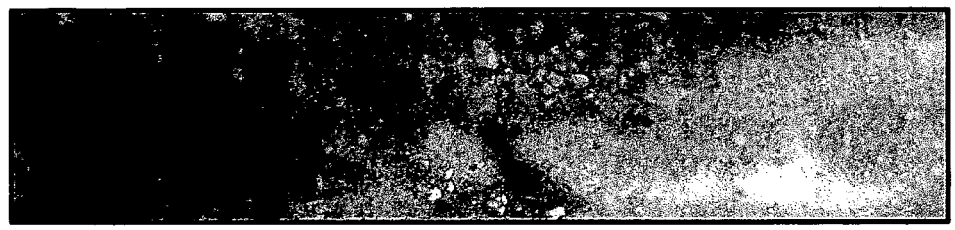
FIG. 4b illustrates the image obtained for a Carbopol containing formulation of the present invention.
Figure 5:
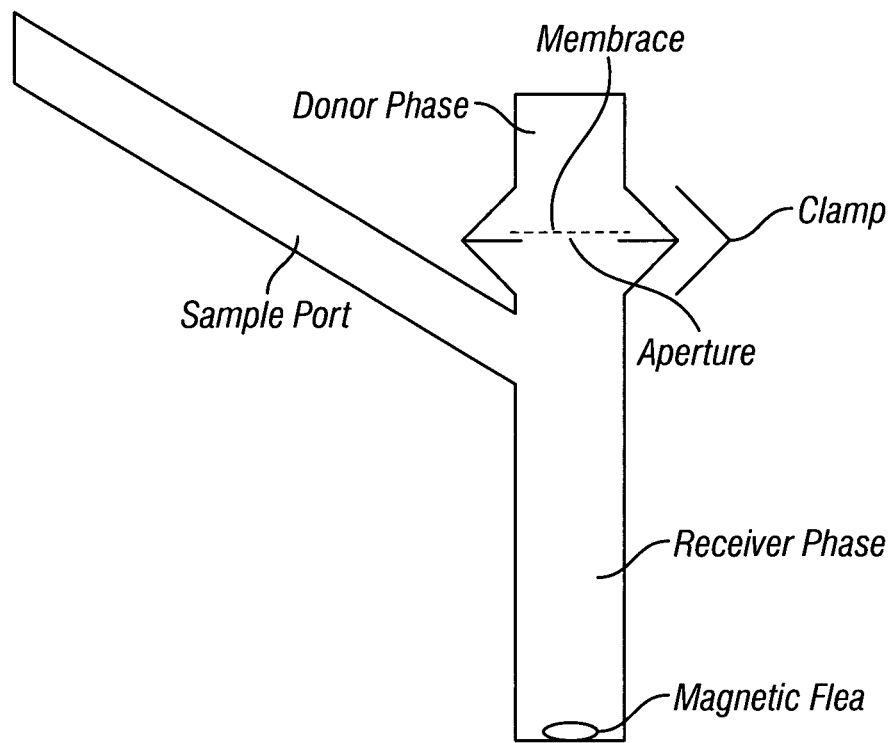
FIG. 5 illustrates a FRANZ cell used to determine the ability of the formulation to deliver an active pharmaceutical agent locally.
Figure 6:
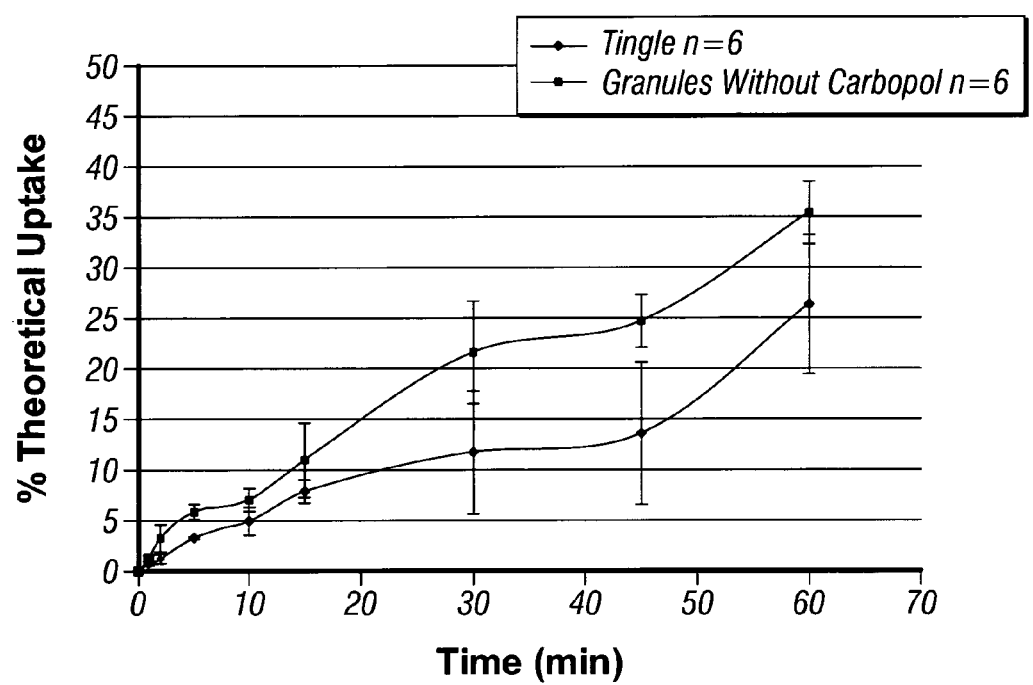
FIG. 6 illustrates the results obtained using the FRANZ cell.

The components and quantitative amounts of the composition are shown in the following Tables:

Example 1

| Component | Quantity (mg) | Function |
| --- | --- | --- |
| Flurbiprofen | 8.750 | Active ingredient |
| Xylitol CM170 | 315.000 | Diluent |
| Mannitol 100SD | 384.945 | Diluent |
| Carbomer 974P | 25.500 | Bioadhesive/ Granulation aid |
| Sodium bicarbonate, medium granule | 63.750 | Effervescent |
| Cool Mix for Mint 506070 TP0504 | 19.670 | Flavour |
| Peppermint 201500 TP0504 | 5.100 | Flavour |
| Aspartame | 4.250 | Sweetener |
| Citric acid anhyrous | 21.250 | Effervescent |
| Silicon dioxide | 1.785 | Flow aid |
| Total | 850.00 | |

Example 2

| Component | Quantity (mg) | Function |
| --- | --- | --- |
| Flurbiprofen | 8.750 | Active ingredient |
| Xylitol CM170 | 315.000 | Diluent |
| Mannitol 100SD | 359.945 | Diluent |
| Carbomer 974P | 25.500 | Bioadhesive/ Granulation aid |
| Sodium bicarbonate, medium granule | 63.750 | Effervescent |
| Flavour | 24.770 | Flavour |
| Aspartame | 4.250 | Sweetener |
| Citric acid anhyrous | 21.250 | Effervescent |
| Sodium Chloride | 25.000 | Excipient |
| Silicon dioxide | 1.785 | Flow aid |
| Total | 850.00 | |

Example 3

| Component | Quantity (mg) | Function |
| --- | --- | --- |
| Flurbiprofen | 8.750 | Active ingredient |
| Xylitol CM170 | 315.000 | Diluent |
| Mannitol 100SD | 384.945 | Diluent |
| Carbomer 974P | 25.500 | Bioadhesive/Granulation aid |
| Sodium bicarbonate, medium granule | 63.750 | Effervescent |
| Flavour | 24.770 | Flavour |
| Aspartame | 4.250 | Sweetener |
| Citric acid anhyrous | 21.250 | Effervescent |
| Silicon dioxide | 1.785 | Flow aid |
| Total | 850.00 | |

Flurbiprofen is a potent non-steroidal anti-inflammatory drug (NSAID), which has been shown to be efficacious in the treatment of sore throat in a number of phase II and phase III clinical studies.

Xylitol and mannitol are widely employed as pharmaceutical diluents. They also exhibit a cooling effect on dissolution in the mouth.

Carbomer is used in pharmaceuticals as a thickening or gelling agent, and forms very high viscosity gels at low concentrations and has good film forming properties. However, in the formulation of the present invention the primary role is to give a coating sensation when the product dissolves in the mouth. The excipient is also used as a granulation aid and helps hold the ingredients together and therefore producing a more durable granule. The carbomer also holds the components together, preferably in a form which flows, and yet which substantially does not release into the air fine particulates, i.e. "dust", which could cause a patient to cough or choke.

Sodium bicarbonate and citric acid enable the product to effervesce.

In order to optimise the flow of the blend during granule manufacture and packing, silicon dioxide, a flow aid, was added. Silicon dioxide also acts as a moisture scavenger, thereby minimising moisture up take from the product ingredients.

The granule is manufactured with a high shear granulation technique using purified water for the process solvent. The wet mass is fluid bed dried to constant percent weight by weight moisture content then milled through a serrated screen to produce a more uniform particle size.

The flavours, aspartame, citric acid and silicon dioxide are blended into the milled granules and then packed into aluminium foil stick packs to produce the final product.

The following particulate composition was prepared as follows:

Flurbiprofen, xylitol, mannitol, carbomer and sodium bicarbonate are sieved through a 1000 μm screen and then pre-mixed using a tumble blend technique. The blended powders are then granulated with 4.5% w/w purified water for three minutes using a PMA150 (GEA) granulator.

The wet granule mass is then transferred into a T/SG3 (GEA) fluid bed drier and dried for 15 minutes at a temperature of 55° C. with the airflow set at 500 m³/h.

The resulting dried granule mass is milled through a serrated screen to produce a uniform granule particle size.

The cool mix for mint and peppermint flavours, aspartame, citric acid and silicon dioxide are sieved through a 1000 μm screen and then mixed with the milled flurbiprofen granules using a ribbon blending technique. The resulting blend is stored in a polythene lined container.

Before packing, the bulk granule blend is mixed for 10 minutes using a tumble blend technique to ensure that no segregation of the product has occurred during transport from manufacture to packing areas.

The granules are transferred into the packing line hopper and then 0.85 grams is filled into individually formed stick packs.

In use the formulation is poured into the mouth and the granules start to effervesce. It is believed that when the granules are placed in the mouth, the effervescence (citric acid/bicarbonate reaction) provides the necessary shear force to effectively extend and fully hydrate the carbopol, providing an aqueous dispersion in a short time. The product is then immediately swallowed, as a semi-gelled aerated mass of saliva and polymer, with the active constituent (flurbiprofen) in dissolution/suspension. It is believed that the carbopol gel will adhere to the throat surface as it is swallowed, and form an adherent film or gel layer. In this layer the flurbiprofen dose will be retained and localised, rather than immediately transferred to the stomach by swallowing. This localisation permits a local (topical) action of flurbiprofen on the throat tissues. It is also believed that the gel layer reduces the irritation in the throat, and provides a soothing sensation by physical means in addition to the pharmacological (antiinflammatory) action of the flurbiprofen.

The bioadhesion and active delivery of the formulations prepared in the Examples were tested for using an IVOR model and a FRANZ cell. The IVOR model, FRANZ cell and results obtained therefrom are illustrated in the Figures.

The IVOR model was designed to enable the granule to be added on a platform at the top of the slope to mimic the mouth/tongue. Artificial saliva applied in at intervals was used to wash the product and simulate natural swallowing action. (30° slope to 15° slope). Using the in vitro oesophageal retention model the retention profiles for the active flurbiprofen was determined over a period of 90 minutes.

A comparison was made between formulae with and without Carbopol and against a marketed lozenge product containing the same amount of flurbiprofen per sample.

The retention profiles shows differences in surface adhesion between the alternative formats. Overall the profile of the lozenge and the granule samples can be described as fast initial active release (75% after 5 minutes) followed slow residual active release (greater for the formulation of the present invention than for lozenges or granules without Carbopol)

At 90 minutes approx. 100% of the flurbiprofen has been release from the surface for all samples The addition of Carbopol to the formulation enhances retention on the model surface and still allows the active to be released in a timeframe suitable for the treatment of sore throats. The control formulation without Carbopol will not adhere to the target surface and does not slow the release of the active as much as the formulation of the present invention.

The data from the FRANZ cell demonstrates that the inclusion of bioadhesive polymers retards the release and transport of flurbiprofen ensuring that the localised target (surface adhered to) receives a continuous and long lasting dose.

A formulation without such properties will deliver the active flurbiprofen immediately and as a result the majority of the pain relief action will be systemic rather than localised.

The formulation of the present invention ensures that bioadhesion takes place in target area throat, and that that actives retained in formulation are (1) retained as part of bioadhesive function in target area and (2) the retained actives are able to dissociate from the bioadhesive into surrounding volume in a suitable timeframe.

Further modifications and developments can be made without departing from the scope of the invention described herein.

The invention claimed is:

1. An ingestible particulate composition comprising:
   at least one pharmaceutically active compound selected from the group consisting of 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine;
   one or more bioadhesive materials present in an amount up to 10 wt %;
   sodium bicarbonate; and
   citric acid;
   wherein a mean particle size of the particulate composition is not greater than 1.0 mm.

2. A composition according to claim 1, wherein the composition is a flowable particulate.

3. A composition as claimed in claim 1, wherein the at least one pharmaceutically active compound is selected from the group consisting of 2,4-dichlorobenzyl alcohol, amylmetacresol, hexylresorcinol, and flurbiprofen.

4. A composition as claimed in claim 3, wherein the at least one pharmaceutically active compound is flurbiprofen.

5. A composition as claimed in claim 1, wherein the one or more bioadhesive materials is a polymeric or oligomeric compound.

6. A composition as claimed in claim 1, further comprising a flow-aid.

7. A composition according to claim 1, for use in a method of treatment of a human or animal body by therapy.

8. A single-pack dosage form comprising a single dose of a composition of claim 1, the single-pack dosage form being a targeted outlet pack which necessarily deposits the composition onto a small area within the mouth.

9. A single-pack dosage form according to claim 8, being a stick-form sachet.

10. A bulk pack comprising a bulk source of a composition of claim 1, together with dosage metering means or dosage information.

11. A method of making a medicament for the treatment of sore throat comprising forming a composition according to claim 1 by combining at least one pharmaceutically active compound and one or more bioadhesive materials.

12. A method of treating sore throat comprising:
   administering a flowable particulate composition into a mouth of a patient, the composition comprising:
   at least one pharmaceutically active compound selected from the group consisting of 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine;
   one or more bioadhesive materials present in an amount up to 10 wt %;
   sodium bicarbonate; and
   citric acid;
   wherein a mean particle size of the particulate composition is not greater than 1.0 mm.

13. A method of making of a particulate composition suitable for pouring into a mouth of a patient comprising forming a composition comprising:
   at least one pharmaceutically active compound selected from the group consisting of 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine;
   one or more bioadhesive materials present in an amount up to 10 wt %;
   sodium bicarbonate; and
   citric acid;
   wherein a mean particle size of the particulate composition is not greater than 1.0 mm.

14. A targeted outlet pack containing a single dose of an ingestible flowable particulate composition, the targeted outlet pack being adapted to deposit the composition onto a small area within the mouth, the composition comprising:
   at least one pharmaceutically active compound selected from the group consisting of 2,4-dichlorobenzyl alcohol, amylmetacresol, cetylpyridinium chloride, hexitidine, hexylresorcinol, flurbiprofen, lidocaine, benzocaine, ibuprofen, paracetamol, pectin, menthol, and benzydamine;
   one or more bioadhesive materials present in an amount up to 10 wt %;
   sodium bicarbonate; and
   citric acid;
   wherein a mean particle size of the particulate composition is not greater than 1.0 mm.

15. A composition according to claim 1, wherein the composition further comprises an organic acid.

16. A composition as claimed in claim 5, wherein the polymeric or oligomeric compound has high a molecular weight up to several million Daltons.

17. A composition according to claim 7, for use in a method of treatment of sore throats.

* * * * *